US007956047B2

(12) United States Patent  
Aspberg et al.

(10) Patent No.: US 7,956,047 B2  
(45) Date of Patent: Jun. 7, 2011

(54) USE OF CHONDROITIN SULPHATE E (CS-E) FOR THE TREATMENT OF DISEASES OR CONDITIONS RELATED TO COLLAGEN FIBRIL FORMATION

(75) Inventors: Anders Aspberg, Lund (SE); Dick Heinegård, Lund (SE); Anna Johnson, Lund (SE); Alexander Kvist, Lund (SE)

(73) Assignee: AnaMar AB, Gothenburg (SE)

( * ) Notice: Subject to any disclaimer, the term of this patent is extended or adjusted under 35 U.S.C. 154(b) by 0 days.

(21) Appl. No.: 11/587,675

(22) PCT Filed: Apr. 26, 2005

(86) PCT No.: PCT/SE2005/000599
§ 371 (c)(1),
(2), (4) Date: Dec. 17, 2007

(87) PCT Pub. No.: WO2005/102362
PCT Pub. Date: Nov. 3, 2005

(65) Prior Publication Data  
US 2008/0200426 A1    Aug. 21, 2008

(30) Foreign Application Priority Data  
Apr. 26, 2004 (SE) .................................. 0401069

(51) Int. Cl.  
A01N 43/04 (2006.01)  
A61K 31/715 (2006.01)  
A61K 31/737 (2006.01)  
C07H 1/00 (2006.01)  
A61P 19/00 (2006.01)

(52) U.S. Cl. .................... 514/54; 514/925; 536/123.1  
(58) Field of Classification Search ............... 514/54, 514/925; 536/123.1  
See application file for complete search history.

(56) References Cited

U.S. PATENT DOCUMENTS

| 5,929,050 | A | 7/1999 | Petito |
| 5,955,578 | A | 9/1999 | Pierschbacher et al. |
| 6,162,787 | A | 12/2000 | Sorgente et al. |
| 6,372,794 | B1 | 4/2002 | Nimni |
| 6,599,888 | B1 | 7/2003 | Derrieu et al. |
| 2003/0069205 | A1 | 4/2003 | Roufa et al. |

FOREIGN PATENT DOCUMENTS

| CA | 2493639 | | 2/2004 |
| JP | 10-120577 | | 5/1998 |
| JP | 2004-059506 | * | 2/2004 |
| JP | 2004-210715 | | 7/2004 |
| RU | 2216332 | | 11/2003 |
| WO | WO 91/15216 | | 10/1991 |
| WO | WO 01/93846 | | 12/2001 |
| WO | WO 02/33085 | | 4/2002 |
| WO | WO 2005/102362 | | 11/2005 |

OTHER PUBLICATIONS

Boyd, J. (2007) Rice Breakthrough Aims to Prevent Fibrotic Diseases. The Magazine of Rice University, vol. 63, No. 3.*
Kadler, K.E. (1996) Collagen fibril formation. Biochemical Journal, vol. 316, p. 1-11.*
Kvist, A.J., Johnson, A.E., Mörgelin, M., Gustafsson, E., Bengtsson, E., Lindblom, K., Aszódi, A., Fässler, R., Sasaki, T., Timpi, R., Aspberg, A. (2006) Chondroitin Sulfate Perlecan Enhances Collagen Fibril Formation, Implications for Perlecan Chondrodysplasias. Journal of Biological Chemistry, vol. 281, No. 44, p. 33127-33139.*
Kasavina, B.S., Rikhter, A.I., Zenkevich, G.D. (1961) The Effect of Chondroitin Sulfate (Chonsuridum) on collagen In Vivo. Bulletin of Experimental Biology and Medicine, vol. 51, No. 6, p. 718-720.*
Nagaoka, T., Kaburagi, Y., Hamaguchi, Y., Hasegawa, M., Takehara, K., Steeber, D.A., Tedder, T.F., Sato, S. (2000) Delayed Wound Healing in the Absence of Intercellular Adhesion Molecule-1 or L-Selectin Expression. American Journal of Pathology, vol. 157, No. 1, p. 237-247.*
Definition of "ulcer" from The Free Dictionary [online], [retrieved on Dec. 8, 2009]. Retrieved from the internet <http://medical-dictionary.thefreedictionary.com/ulcers>.*
Peyton, B.D., Rohrer, M.J., Furman, M.I., Barnard, M.R., Rodino, L.J., Benoit, S.E., Hechtman, H.B., Valeri, R., Michelson, A.D. (1998) Patients with venous stasis ulceration have increased monocyte-platelet aggregation. Journal of Vascular Surgery, vol. 27, No. 6, p. 1109-1116.*
Essentials of Glycobiology (1999) Edited by Varkit, A., Cummings, R., Esko, J., Freeze, H., Hart, G., Marth, J. Published by Cold Spring Harbor Laboratory Press, New York, p. 26-28.*
Danielson, K. et al., Targeted Disruption of Decorin Leads to Abnormal Collagen Fibril Morphology and Skin Fragility. The Journal Cell Biology Feb. 10, 1997;136(3):729-743.
Hedbom, E. and Heinegard, D., Interaction of a 59-kDa Connective Tissue Matrix Protein with Ciollagen I and Collagen II. The Journal of Biological Chemistry Apr. 25, 1989; 264(12)6898-6905.
Svensson, L. et al., Fibromodulin-null Mice Have Abnormal Collagen Fibrils, Tissue Organization, and Altered Lumican Deposition in Tendon. The Journal of Biological Chemistry Apr. 2, 1999;274(14):9636-9647. Vogel, K. et al., Specific Inhibition of Type I and Type II Collagen Fibrillogenesis by the Small Proteoglycan of Tendon. Biochem. J. Feb. 29, 1984;223:587-597.
Einbinder et al. "Separation of chondroitin sulphate from cartilage" *J. Biol. Chem.* (1950) 185:725-730.
Adebowale et al. "Analysis of glucosamine and chondroitin sulfate content in marketed products and the Caco-2 permeability of chondroitin sulfate raw materials" *J. Am. Nutr. Assoc.* (2000) 3:37-44.
Sugahara et al. "Structure and Function of Oversulfated Chondroitin Sulfate Variants: Unique Sulfation Patterns and Neuroregulatory Activities" *Trends in Glycoscience and Glycotechnology* (2000) 12(67):321-349.
Yamada et al. "Potential Therapeutic Application of Chondroitin Sulfate/Dermatan Sulfate" *Current Drug Discovery Technologies* (2008) 5(4):289-301.
Steffensen et al., "Proteolytic events of wound-healing-coordinated interactions among matrix metalloproteinases (MMPs), integrins, and extracellular matrix molecules", Crit. Rev. Oral. Biol. Med. (2001) 12(5): 373-398.

(Continued)

Primary Examiner — Shaojia Anna Jiang  
Assistant Examiner — Scarlett Goon  
(74) Attorney, Agent, or Firm — Wolf, Greenfield & Sacks, P.C.

(57) ABSTRACT

The present invention comprises the use of chondroitin sulphate (CS-E) or an active fragment thereof for the treatment of diseases or conditions related to collagen fibril formation. Said compounds can be administered either by oral, topical, injectable or by any other suitable route.

18 Claims, 2 Drawing Sheets

OTHER PUBLICATIONS

Arikawa-Hirasaw et al., "Perlecan is Essential for Cartilage and Cephalic Development," *Nature Genetics* 23:354-358 (1999).

Aviezer et al., "Perlecan, Basal Lamina Proteoglycan, Promotes Basic Fibroblast Growth Factor-Receptor Binding, Mitogenesis, and Angiogenesis," *Cell* 79:1005-1013 (1994).

Bengtsson et al., "The Leucine-Rich Repeat Protein PRELP Binds Perlecan and Collagens and May Function as a Basement Membrane Anchor," *The Journal of Biological Chemistry* 277(17):15061-15068 (2002).

Brown et al., "The C-Terminal Domain V of Perlecan Promotes β1 Integrin-Mediated Cell Adhesion, Binds Heparin, Nidogen and Fibulin-2 and Can Be Modified by Glycosaminoglycans," *Eur. J. Biochem* 250:39-46 (1997).

Costell et al., "Perlecan Maintains the Integrity of Cartilage and Some Basement Membranes," *The Journal of Cell Biology* 147(5):1109-1122 (1999).

Couchman et al., "Perlecan and Basement Membrane-Chondroitin Sulfate Proteoglycan (Bamacan) are Two Basement Membrane Chondroitin/Dermatan Sulfate Proteoglycans in the Engelbreth-Holm-Swarm Tumor Matrix," *The Journal of Biological Chemistry* 271(16):9595-9602 (1996).

Gonzalez et al., "A Novel Interaction Between Perlecan Protein Core and Progranulin," *The Journal of Biological Chemistry* 278(40):38113-38116 (2003).

Heinegard and Paulsson, "Structure and Metabolism of Proteoglycans," Extracellular Matrix Biochemistry $1^{st}$ Edition, Elsevier, Amsterdam, Chapter 8: 277-328 (1984).

Nicole et al., "Perlecan, the Major Proteoglycan of Basement Membranes, is Altered in Patients with Schwartz-Jampel Syndrome (Chondrodystrophic Myotonia)," *Nature Genetics* 26:480-486 (2000).

Timpl and Brown, "Supramolecular Assembly of Basement Membranes," *BioEssays* 18(2):123-132 (1995).

Wight et al., "Proteoglycans" Cell Biology of Extracellular Matrix, Second Edition, Plenam Press, New York, Chapter 2: 45-78 (1991).

Powell, et al.; "Chronic venous insufficiency is associated with increased platelet and monocyte activation and aggregation"; Journal of Vascular Surgery (1999); 30(5): 844-853.

Bocker, T. et al., Synthesis and properties of sulfated alkyl glycosides. Carbohydr Res. Jun. 16, 1992;230(2):245-56.

Edward, M. and Oliver, R.F., Changes in the synthesis, distribution and sulphation of glycosaminoglycans of cultured human skin fibroblasts upon ascorbate feeding. J Cell Sci. Nov. 1983;64:245-54.

Gilbert, M.E. et al., Chondroitin sulfate hydrogel and wound healing in rabbit maxillary sinus mucosa. Laryngoscope. Aug. 2004;114(8):1406-9.

Habuchi, O. et al., Enzymatic synthesis of chondroitin sulfate E by N-acetylgalactosamine 4-sulfate 6-O-sulfotransferase purified from squid cartilage. Anal Biochem. Nov. 15, 2002;310(2):129-36.

Integra™ website: http://www.integra-ls.com/products/?product=122 (Integra™ Bilayer Matrix Wound Dressing), [Retrieved from the internet on Nov. 12, 2007].

Kaji, T. et al., Characterization of chondroitin/dermatan sulfate proteoglycans synthesized by bovine retinal pericytes in culture. Biol Pharm Bull. Nov. 2004;27(11):1763-8.

Karamanos, N.K. et al., Isolation and chemical study of the glycosaminoglycans from squid cornea. Int J Biochem. 1991;23(1):67-72.

Kirker, K.R et al., Glycosaminoglycan hydrogels as supplemental wound dressings for donor sites. J Burn Care Rehabil. May-Jun. 2004;25(3):276-86. (Abstract).

Kirker, K.R. et al., Glycosaminoglycan hydrogel films as bio-interactive dressings for wound healing. Biomaterials. Sep. 2002;23(17):3661-71.

Kosir, M.A. et al., Matrix glycosaminoglycans in the growth phase of fibroblasts: more of the story in wound healing. J Surg Res. Jul. 2000;92(1):45-52.

Munakata, H. et al., Interaction between collagens and glycosaminoglycans investigated using a surface plasmon resonance biosensor. Glycobiology. Oct. 1999;9(10):1023-7.

Nemeth-Csoka, M. and Kovacsay, A., The effect of glycosaminoglycans on the in vitro fibril formation of collagen type I and type III. Exp Pathol (Jena). 1979;17(2):82-7.

Ruszczak, Z., Effect of collagen matrices on dermal wound healing. Adv Drug Deliv Rev. Nov. 28, 2003;55(12):1595-611. Review.

Shen, B. et al., Biosensor analysis of the molecular interactions of pentosan polysulfate and of sulfated glycosaminoglycans with immobilized elastase, hyaluronidase and lysozyme using surface plasmon resonance (SPR) technology. J Pharm Biomed Anal. Feb. 5, 2003;31(1):83-93.

Stallcup, W.B. and Dahlin-Huppe, K., Chondroitin sulfate and cytoplasmic domain-dependent membrane targeting of the NG2 proteoglycan promotes retraction fiber formation and cell polarization. J Cell Sci. Jun. 2001;114(Pt 12):2315-25.

Sugumaran, G. and Silbert, J.E., Biosynthesis of chondroitin sulfate. Organization of sulfation. J Biol Chem. Mar. 5, 1989;264(7):3864-8.

Tsuchida, K. et al., Appican, the proteoglycan form of the amyloid precursor protein, contains chondroitin sulfate E in the repeating disaccharide region and 4-O-sulfated galactose in the linkage region. J Biol Chem. Oct. 5, 2001;276(40):37155-60. Epub Jul. 30, 2001.

Tully, S.E. et al., A chondroitin sulfate small molecule that stimulates neuronal growth. J Am Chem Soc. Jun. 30, 2004;126(25):7736-7.

Werner, S. and Grose, R., Regulation of wound healing by growth factors and cytokines. Physiol Rev. Jul. 2003;83(3):835-70. Review.

Zou, X.H. et al., Chondroitin sulfate in palatal wound healing. J Dent Res. Nov. 2004;83(11):880-5.

\* cited by examiner

Figure 2 CS-E accelerated collagen fibril formation.
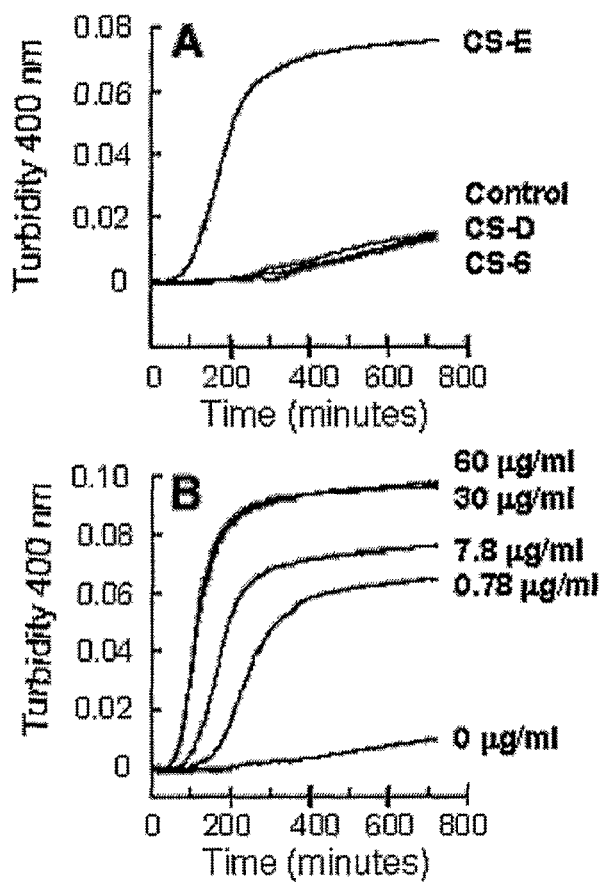

USE OF CHONDROITIN SULPHATE E (CS-E) FOR THE TREATMENT OF DISEASES OR CONDITIONS RELATED TO COLLAGEN FIBRIL FORMATION

TECHNICAL BACKGROUND

Many proteins of the extracellular matrix (ECM) are modified post-translationally by addition of oligosaccharide chains and are thus known as glycoproteins. The oligosaccharides are linked either O-glycosidically to serine or threonine residues, or N-glycosidically to an asparagine residue. Proteoglycans are glycoproteins that are substituted with a particular class of carbohydrate polymers, known as the glycosaminoglycans (GAGs). Proteoglycans are found in the ECM, at the cell surface and intracellularly in storage granules. In the ECM they contribute to the structure and organisation, and at the cell surface often function as receptors and/or co-receptors. All glycosaminoglycans (with the exception of hyaluronan) are synthesised on a core protein acceptor, and they are thus an integral component of proteoglycans (Wight et al., 1981; Heinegård and Paulsson, 1984, review).

Glycosaminoglycans (GAGs) are named to indicate that one of the monosaccharides in the repeating sequence of disaccharides is an amino sugar. The other monosaccharide is an uronic acid (glucuronic acid or iduroic acid), with the exception of keratan sulphate where it is a galactose. While other oligosaccharide substituents may be branched, GAG chains are linear (again, with the exception of keratan sulphate). Proteoglycans may be substituted with one (e.g. decorin) and up to some one hundred (e.g. aggrecan) GAG chains.

There are 4 types of glycosaminoglycans: hyaluronic acid, chondroitin sulphate/dermatan sulphate, heparan sulphate/heparin and keratan sulphate. The disaccharides in all glycosaminoglycan chains except hyaluronan are sulphated, increasing their negative charge and leading to an extended conformation of the chain. The molecule will occupy large solvent domains, observed as a high viscosity of a solution. This property is essential in cartilage and is the basis on which the tissue's resistance lies.

The repeating disaccharide sequence in CS is glucuronic acid-N-acetyl-galactosamine (GlcA-GalNAc), see FIG. 1. Chondroitin sulphate is found in several forms, named chondroitin-4 sulphate, -6 sulphate and -D and -E respectively. These forms differ in the sulphation of saccharides. CS-E is a highly sulphated species, which is attached to perlecan in the I and V domains.

FIG. 1. Basic structure of Chondroitin sulfate. Repeating dimeric ullits of GlcA β1-3 GalNAc. All hydroxy positions may be sulfated or/and epimerised.

The various positions open for sulfatation are numbered.

Chondroitin sulphate/dermatan sulphate is found in all extracellular matrices. Cartilage and invertebral disc are the tissues richest in chondroitin sulphate (Wight et al., 1981, review). Chondroitin sulphate is synthesised by specific enzymes located in the Golgi. The polymers are assembled onto a linker tri-saccharide. The hydroxyl group of serine residues followed by a glycine in the protein is substituted with a xylose and two successive galactose residues. Thereafter alternating monosaccharides of glucuronic acid and N-acetylgalactosamine are added successively to form the chain. Some glucuronate residues are converted to iduronate by an epimerase and sulfation is the last event just prior to secretion (Wight et al., 1981, review). In cartilage aggrecan, a member of the family hyalectins, is a chondroitin sulphate proteoglycan and is substituted with some one hundred CS chain and some thirty keratan sulphate chains. Aggrecan molecules are clustered along HA strands bound via their N-terminal globular domain. A protein known as link protein contacts both the HA-binding G1 domain of the aggrecan molecule and HA, and stabilises the complex. In this manner hundreds of aggrecan molecules are joined at one end to the HA. Thus, in cartilage matrix chondroitin sulphate is by far the most abundant GAG.

Perlecan was first identified as a large heparan sulphate proteoglycan isolated from the Engelbrecht-Holm-Swarm (EHS) murine basement membrane tumour. In basement membranes, it has been shown to bind several different classes of molecules. In each instance the core protein, the heparan sulphate (HS) side chains or both in concert, are involved in mediating the interaction. The proteoglycan binds to extracellular matrix components integral to basement membrane such as collagen IV, nidogen, laminin, and fibronectin (Timpl, R. and Brown, J. C. (1996) *Bioassays* 18, 123-132). Perlecan has also been shown to bind extracellular matrix components outside the basement membrane, e.g. PRELP and collagen type I (Bengtsson, E., Mörgelin, M., Sasaki, T., Timpl, R., Heinegård, D., and Aspberg, A. (2002) *J. Biol. Chem*). Perlecan supports cell-attachment both by binding and clustering integrins (Brown, J. C., Sasaki, T., Gohring, W., Yamada, Y., and Timpl, R. (1997) *Eur. J Biochem.* 250, 39-46). Binding to growth factors has been shown for both the HS side-chains (FGF-2 (Aviezer, D., Hecht, D., Safran, M., Eisinger, M., David, G., and Yayon, A. (1994) *Cell* 79, 1005-1013)) and the core protein (progranulin, (Gonzalez, E. M., Mongiat, M., Slater, S. J., Baffa, R., and Jozzo, R. V. (2003) *J Biol Chem*)). Based on its interactions, perlecan is assumed to have a role in basement membrane integrity.

Perlecan was originally thought to be substituted with HS exclusively, but later studies revealed that it is also present in a variant partially substituted with chondroitin sulphate (CS) (Couchman, J. R., Kapoor, R., Sthanam, M., and Wu, R. R. (1996) *J Biol Chem* 271, 9595-9602). Both the HS- and the HS/CS-substituted variants of perlecan have been found in tissues other than basement membrane, for example cartilage.

The generation of perlecan null mice revealed two particularly intriguing findings (Arikawa-Hirasawa, E., Watanabe, H., Takani, H., Hassell, J. R., and Yamada, Y. (1999) *Nat Genet.* 23, 354-358; Costell, M., Gustafsson, E., Aszódi, A., Morgelin, M., Bloch, W., Hunziker, E., Addicks, K., Timpl, R., and Fässler, R. (1999) *J Cell Biol* 147, 1109-1122). First, though mice lacking perlecan did develop grave disorders caused by compromised basement membrane strength or integrity (e.g. rupture of pericardial sac), the initial assembly of basement membranes seemed to be without complication. The second striking finding was the severe skeletal defects exhibited, apparently caused by the lack of perlecan in cartilage.

Following the publication of these results at least two human hereditary diseases with skeletal deficiencies have been ascribed to an underlying scarcity or complete lack of perlecan, underscoring the relevance of this finding in the mouse model (Nicole, S., Davoine, C. S., Topaloglu, H., Cattolico, L., Barral, D., Beighton, P., Hamida, C. B., Hammouda, H., Cruaud, C., White, P. S., Samson, D., Urtizberea, J. A., Lehmann-Horn, F., Weissenbach, J., Hentati, F., and Fontaine, B. (2000) *Nat Genet.* 26, 480-483; Arikawa-Hirasawa, E., Wilcox, W. R., Le, A. H., Silverman, N., Govindraj, P., Hassell, J. R., and Yamada, Y. (2001) *Nat Genet.* 27, 431-434).

In skeletal development, the deposition of a cartilaginous template precedes the formation of bones. The integrity of this template is a prerequisite for proper assembly of the skeleton. Perlecan-null mouse cartilage shows fewer and less organised collagen type II fibrils, and decreased levels of aggrecan, indicating a failure to organise the extracellular matrix (Costell, M., Gustafsson, E., Aszódi, A., Morgelin, M., Bloch, W., Hunziker, E., Addicks, K., Timpl, R., and Fäqssler, R. (1999) *J Cell Biol* 147, 1109-1122).

Mature collagen fibres may contain several different types of bound accessory proteins. They are part in the organisation of these fibres and regulate links to other molecules thereby contributing to the architecture of the fibrillar collagen network. A recent concept is that of modulator molecules, which regulate the early steps in the assembly of collagen monomers to fibres. Our laboratory has found that cartilage oligomeric matrix protein (COMP) accelerates the formation of fibres from monomers (Mörgelin and Heinegård, manuscript). Other molecules have the opposite effect and slow down fibre formation in vitro, e.g. decorin (Vogel, K. G., Paulsson, M., and Heinegård, D. (1984) *Biochem. J.* 223, 587-597) and fibromodulin (Hedbom, E. and Heinegård, D. (1989) *J. Biol. Chem.* 264, 6898-6905). Gene targeting of these molecules lead to abnormal collagen fibrils and disturbed mechanical properties of the tissues (Danielson, K. G., Baribault, H., Holmes, D. F., Graham, H., Kadler, K. E., and Iozzo, R. V. (1997) *J Cell Biol* 136, 729-743; Svensson, L., Aszódi, A., Reinholt, F. P., Fäissler, R., Heinegård, D., and Oldberg, Å. (1999) *J. Biol. Chem.* 274, 9636-9647). A picture is emerging where proteins in the vicinity of the cell regulate the early stages of collagen fibre formation.

Perlecan exists as HS and CS substituted forms and it has been shown that these forms can be used to facilitate collagen fibril formation. To our surprise, the addition of free CS-E was effective in collagen fibril formation, but none of the other CS variants had any significant effect (e.g. CS-D or CS-6).

A number of publications describing the effect of chondroitin sulphate on wound healing and for treating arthrosis exist (U.S. Pat. No. 5,929,050, JP10120577 and RU2216332). The present invention differs from these significantly as the use of CS-E or active fragments thereof stimulates the formation of collagen based extracellular matrix (ECM) and thus acting as fibrillogenesis agonists or, by modification of CS-E or active fragments thereof, as fibrosis antagonists.

BRIEF DESCRIPTION OF THE DRAWINGS

FIGS. 2A and 2B show graphs depicting data on CS-E accelerated collagen fibril formation, obtained from a collagen fibrillogenesis assay.

DESCRIPTION OF THE INVENTION

Figure 1:
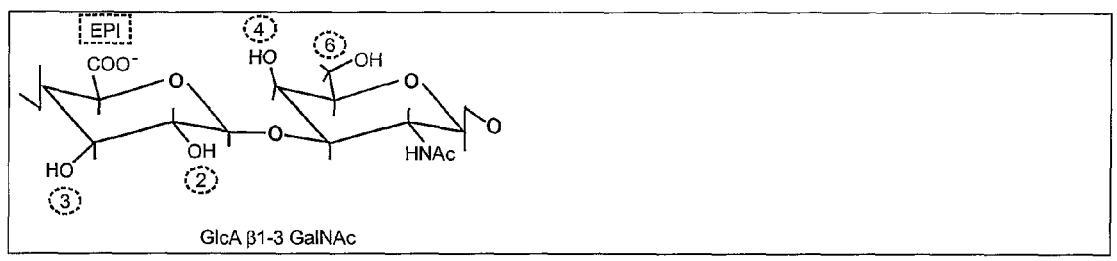
FIG. 1 depicts the basic structure of chondroitin sulfate.

Comprised in the invention is the use of chondroitin sulphate from Perlecan or chondroitin sulphate E (CS-E) or active fragments of CS-E for treatment of various conditions and diseases related to disorders by the facilitation or prevention of collagen fibril formation (CFF) by agonists and antagonists respectively.

Also comprised is a pharmaceutical acceptable composition containing CS-E or active fragments thereof for treating said conditions and diseases.

CS-E or active fragments thereof are highly sulphated and thus may be charged compounds and the invention also comprises pharmaceutical acceptable salts, such as alkali metal salts (sodium, potassium, cesium) and alkaline earth salts (e.g. magnesium, zinc, calcium, strontium) and ammonium, as well as organic salts.

Also comprised in the invention is a formulation for administration of a therapeutically effective amount of CS-E, or active fragments thereof in production of artificial collagen matrices for treatment of disorders by transplantation of cell containing or recruiting scaffolds.

Indications comprised in this application are conditions and diseases related to disorders in collagen fibrillogenesis, including but not limited to pulmonary fibrosis, wound healing, in particular chronic wound healing, chronic intestinal disease such as ulcerative colitis and Crohns disease, rheumatoid arthritis (RA), osteoarthritis (OA), reconstructive skeletal formation and skeletal repair.

CFF Agonists

Chronic wound healing can be stimulated by application of a CFF agonist, alone or together with exogenous collagen. This is also useful for treatment of acute open wounds.

CFF agonists also facilitates healing of internal wounds including but not limited to peptic ulcers, ulcerous colitis, Crohn's disease or other inflammatory bowel disease.

CFF agonists can be used to facilitate healing after surgical treatment and transplantation.

In the progressive degenerative joint disease osteoarthritis the articular cartilage collagen is degraded. CFF agonists counteract or reverse this process and/or facilitates the assembly of newly synthesized collagen molecules into fibers.

CFF agonists can be used to stimulate repair in damaged ligaments and tendons.

CFF agonist can be used to facilitate bone repair after severe fractures.

CFF Agonists in Tissue Engineering

Tissue engineering can be used to repair damaged tissue (e.g. skin in burn wound healing or cartilage in OA) via autologous cell replacement therapy or transplantation. CFF agonists can be used to stimulate collagen matrix formation in cell or tissue culture for production of transplantable skin, tendon, cartilage, bone or blood vessels from patient cells or tissue or from various types of stem cells.

CFF agonists can be used to produce well-formed artificial collagen matrix scaffolds for use in healing of e.g. burn wounds and OA cartilage. After implantation these scaffolds would be populated by cells recruited from the surrounding tissue of the patient.

CFF agonists are also useful in the production of well-organised collagen fibril matrices for corneal implants.

Fibrotic Disorders

Scarring is a natural response of the body to trauma and injury. In fibrotic conditions the normal wound healing response continues out of control, with excessive production and deposition of collagen. This leads to a loss of function when normal tissue is replaced with scar tissue. Fibrosis can affect virtually all organ systems in the body.

There are many different causes of fibrosis, e.g. trauma, surgery, infection, environmental pollutants and toxins (including alcohol). Some examples of fibrotic conditions are formation of scar tissue following heart attack, kidney fibrosis as a complication of diabetes, lung fibrosis and surgical scar tissue formation between internal organs.

Acute fibrosis is a response to various forms of trauma, such as injury, infections, surgery, burns, radiation damage and chemotherapeutic treatments. Many chronic conditions, e.g. diabetes, viral infection and hypertension, induce a progressive fibrosis causing continuous loss of tissue function. The liver, kidney and lung are commonly affected. Systemic fibrotic diseases include diabetic nephropathy, scleroderma, idiopathic pulmonary fibrosis and reactive fibrosis following myocardial infarct.

CFF Antagonists

By using CFF antagonists it will be possible to counteract fibrotic processes by blocking the assembly of the collagen fibrils. In many cases this can be achieved by local administration thus avoiding possible side effects from systemic treatment. However, the CFF antagonists may also be administered systemically when suitable.

CFF antagonists can be used to prevent fibrotic disorders of the skin, including, but not limited to scar formation in wound healing, hypertrophic scarring and keloid, contracture in connection with hypertrophic scarring after burn injury, surgical adherens or scleroderma. Local application of the CFF antagonists would be easy, except in surgical adherens where administration could be achieved by osmotic pump devices or other suitable administrations.

CFF antagonists can be used for treatment and prevention of idiopathic lung fibrosis.

CFF antagonists could be used to treat other deep organ fibrosis such as liver fibrosis/cirrhosis and diabetic kidney fibrosis.

CFF antagonists could be used to prevent heart muscle scarring after myocardial infarction.

CFF antagonists could be used to prevent or counteract atherosclerosis and restenosis after angioplasty. To achieve the latter, the antagonist could be delivered locally by implantation of modified stents.

EXAMPLES

In Vitro Fibrillogenesis Assay

Bovine pepsin-extracted collagen type I was purchased from Vitrogen. Collagen II was pepsin extracted from bovine tracheal cartilage, as previously described (Vogel, K. G., Paulsson, M., and Heinegård, D. (1984) *Biochem. J.* 223, 587-597). The fibrillogenesis assay has been previously described (Hedborn, E. and Heinegård, D. (1989) *J. Biol. Chem.* 264, 6898-6905).

Briefly, a solution of collagen monomers (330 nM) was brought to neutral pH by addition of an appropriate volume of 0.012M NaOH, and buffered by 20 mM HEPES, 150 mM NaCl at pH 7.4. Perlecan fragment was added at concentrations equimolar to that of collagen or at one tenth the molar concentration of collagen. The sample was mixed vigorously and briefly, and transferred to a cuvette. The sample was incubated at 37° C. (collagen type I) or 35° C. (collagen type II) in water-jacketed cuvettes in the spectrophotometer, and the absorbance due to light scattering at 400 nm (collagen type I) or 313 nm (collagen type II) was monitored over a duration of 5-18 hrs. The increased absorbance/turbidity depends on increasing fibre formation.

CS-E Fibrillogenesis

Fibrillogenesis was performed as described above. CS-E from squid was purchased from Calbiochem. 0.13 µg/ml corresponding to the molar concentration of GAG chains in previous experiments using recombinant perlecan domain I variants with HS/CS (PG IB) (33 nM).

The results of the fibrillogenesis experiment is shown in FIG. 2. As can be seen from this figure, CS-E but none of the other tested chondroitin sulphate variants (CS-D and CS-6) gives a positive result on collagen fibril formation (CFF).

FIG. 2 CS-E accelerated collagen fibril formation. Different types of purified CS-chains were tested for effect in the collagen fibrillogenesis assay (panel A). The highly sulphated CS-E had dramatic effects on fibril formation but neither CS-6 nor CS-D had any effect. The stimulatory effect of CS-E was dose-dependent, reaching saturation at concentration of 30 µg/ml (panel B).

In Vivo Model

Example of In Vivo Model for Studying Wound Healing.

Groups of 5 ICR male mice weighing 22±2 gms are used. Under hexobarbital (90 mg/kg, i.p.) anesthesia, the shoulder and back region of each animal is shaved. A sharp punch (ID 12 mm) is used to remove the skin including panniculus carnosus and adherent tissues. The wound area, traced onto clear plastic sheets on days 3, 5, 7, 9 and 11, are quantitated by use of an Image Analyzer (Life Science Resources VISTA, Version 3.0). Test compound and/or vehicle (20 µl, 0.5% carboxymethylcellulose in PBS pH 7.4) is applied topically immediately following injury and once daily thereafter for a total of 10 consecutive days. The wound half closure time ($CT_{50}$) is determined and unpaired Student's t-test is applied for comparison between treated and vehicle group at each measurement time point. Differences are considered statistical significance at $P<0.05$. (Montesinos, M. C., Gadangi, P., Longaker, M., Sung, J., Levine, J., Nilsen, D., Reibman, J., Li, M., Jiang, C. K., Hirschom, R., Recht, P. A., Ostad, E., Levin, R. I. and Crostein, B. N. Wound healing is accelerated by agonists of Adenosine $A_2$ ($G\alpha_s$-linked) receptors. J. Exp. Med. 186: 1615-1620, 1997.)

Formulation

Example of a Preparation Comprising a Capsule

|  | Per capsule |
| --- | --- |
| Active ingredient, as salt | 5 mg |
| Lactose | 250 mg |
| Starch | 120 mg |
| Magnesium stearate | 5 mg |
| Total up to | 385 mg |

In case higher amounts of active ingredient are required, the amount of lactose used may be reduced.

Example of a Suitable Tablet Formulation.

|  | Per tablet |
| --- | --- |
| Active ingredient, as salt | 5 mg |
| Potato starch | 90 mg |
| Colloidal silica | 10 mg |
| Talc | 20 mg |
| Magnesium stearate | 2 mg |
| 5% aqueous solution of gelatine | 25 mg |
| Total up to | 385 mg |

A solution for parenteral administration by injection can be prepared in aqueous solution of a water-soluble pharmaceutically acceptable acid addition salt of the active substance preferably in a concentration of 0.1% to about 10% by weight.

These solutions may also contain stabilising agents, buffering agents and/or gelating agents such as but not limited to hyaluronan, PEG, HPMC, EHEC, to obtain a controlled release and/or elimination.

Example of a Topical Formulation

A gel for topical administration can be prepared an active substance in a concentration of 0.1% to 10% by weight, optionally containing stabilising agents, buffering agents and/or additional gelating agents such as but not limited to hyaluronan, PEG, HMPC, EHEC to obtain controlled release and/or elimination

The invention claimed is:

1. A method of facilitating collagen fibril formation in a wound in a subject, the method comprising administering to said subject an effective amount of chondroitin sulphate E, wherein the chondroitin sulphate E is administered at a concentration of between 0.13 µg/ml and 60 µg/ml.

2. A method as claimed in claim 1, wherein the chondroitin sulphate E is administered at a concentration of between 0.13 µg/ml and 30 µg/ml.

3. A method as claimed in claim 2, wherein the chondroitin sulphate E is administered at a concentration of between 57.8 µg/ml and 30 µg/ml.

4. A method as claimed in claim 1, wherein the effective amount of chondroitin sulphate E is administered by oral, topical, or injectable route.

5. A method as claimed in claim 4, wherein the effective amount of chondroitin sulphate E is administered by topical route.

6. A method as claimed in claim 5, wherein the chondroitin sulphate E is administered in a gel.

7. A method as claimed in claim 4, wherein the chondroitin sulphate E is administered by an oral route.

8. A method as claimed in claim 1, wherein said chondroitin sulphate E is chondroitin sulphate E obtained from squid.

9. A method as claimed in claim 1, wherein a pharmaceutical composition comprising purified chondroitin sulphate E is administered.

10. A method of facilitating collagen fibril formation in an ulcer in a subject, the method comprising administering to said subject an effective amount of chondroitin sulphate E, wherein the chondroitin sulphate E is administered at a concentration of between 0.13 µg/ml and 60 µg/ml.

11. A method as claimed in claim 10, wherein the chondroitin sulphate E is administered at a concentration of between 0.13 µg/ml and 30 µg/ml.

12. A method as claimed in claim 11, wherein the chondroitin sulphate E is administered at a concentration of between 7.8 µg/ml and 30 µg/ml.

13. A method as claimed in claim 10, wherein the effective amount of chondroitin sulphate E is administered by oral, topical or injectable route.

14. A method as claimed in claim 13, wherein the effective amount of chondroitin sulphate E is administered by topical route.

15. A method as claimed in claim 14, wherein the chondroitin sulphate E is administered in a gel.

16. A method as claimed in claim 13, wherein the chondroitin sulphate E is administered by an oral route.

17. A method as claimed in claim 10, wherein said chondroitin sulphate E is chondroitin sulphate E obtained from squid.

18. A method as claimed in claim 10, wherein a pharmaceutical composition comprising purified chondroitin sulphate E is administered.

\* \* \* \* \*

UNITED STATES PATENT AND TRADEMARK OFFICE
CERTIFICATE OF CORRECTION

PATENT NO. : 7,956,047 B2  
APPLICATION NO. : 11/587675  
DATED : June 7, 2011  
INVENTOR(S) : Anders Aspberg et al.

Page 1 of 1

It is certified that error appears in the above-identified patent and that said Letters Patent is hereby corrected as shown below:

At column 7, claim 3, line 11, please delete "57.8" and insert --7.8--

Signed and Sealed this  
Twenty-third Day of August, 2011

David J. Kappos  
*Director of the United States Patent and Trademark Office*